US00PP15429P2

(12) United States Plant Patent
van Rijn

(10) Patent No.: US PP15,429 P2
(45) Date of Patent: Dec. 14, 2004

(54) ***BOUGAINVILLEA* PLANT NAMED 'VERA PINK'**

(50) Latin Name: *Bougainvillea spectabilis*
Varietal Denomination: Vera Pink

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 10/805,578

(22) Filed: Mar. 20, 2004

(51) Int. Cl.[7] ..... A01H 5/00
(52) U.S. Cl. ..... Plt./256
(58) Field of Search ..... Plt./256

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Bougainvillea* plant named 'Vera Pink', characterized by its upright, outwardly spreading and compact growth habit; thornless stems; roughly spherical inflorescences with numerous flowers; and light pink-colored flower bracts.

1 Drawing Sheet

Botanical classification/cultivar designation: *Bougainvillea spectabilis* cultivar Vera Pink.

BACKGROUND OF THE INVENTION

The present Invention relates to a new and distinct cultivar of *Bougainvillea* plant, botanically known as *Bougainvillea spectabilis,* and hereinafter referred to by the name 'Vera Pink'.

The new *Bougainvillea* is a naturally-occurring whole plant mutation of the *Bougainvillea spectabilis* cultivar Vera Deep Purple, disclosed in U.S. Plant Pat. No. 10,950. The new *Bougainvillea* was discovered and selected by the Inventor as a single flowering plant from within a population of plants of the cultivar Vera Deep Purple in a controlled environment in Schipluiden, The Netherlands in July, 2000. The selection of this plant was based on its attractive flower color.

Asexual reproduction of the new cultivar by cuttings at Schipluiden, The Netherlands since Fall, 2000, has shown that the unique features of this new *Bougainvillea* are stable and reproduced true to type in successive generations.

SUMMARY OF THE INVENTION

Plants of the cultivar Vera Pink have not been observed under all possible environmental conditions. The phenotype may vary somewhat with variations in environment such as temperature and/or light intensity without, however, any variance in genotype.

The following traits have been repeatedly observed and are determined to be the unique characteristics of 'Vera Pink'. These characteristics in combination distinguish 'Vera Pink' as a new and distinct cultivar:

1. Upright, outwardly spreading and compact growth habit.
2. Moderate to rapid growth rate.
3. Thornless stems.
4. Roughly spherical inflorescences with numerous flowers.
5. Light pink-colored flower bracts.

Plants of the new *Bougainvillea* differ from plants of the parent cultivar, Vera Deep Purple, primarily in flower bract coloration as plants of the cultivar Vera Deep Purple have purple-colored flower bracts.

Plants of the new *Bougainvillea* differ from plants of the cultivar Vera Lynn, disclosed in a U.S. Plant patent application Ser. No. 10,805,603 filed concurrently, primarily in flower bract coloration as plants of the cultivar Vera Lynn have darker pink-colored flower bracts than plants of the new *Bougainvillea.*

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new *Bougainvillea.*

The photograph at the top of the sheet comprises a side perspective view of a typical plant of 'Vera Pink'.

The photograph at the bottom of the sheet comprises a side perspective view of a typical plant of 'Vera Deep Purple', left, and 'Vera Pink', right.

DETAILED BOTANICAL DESCRIPTION

In the following description, color references are made to The Royal Horticultural Society Colour Chart, 2001 Edition, except where general terms of ordinary dictionary significance are used. Plants used for the above-mentioned photographs and botanical description were grown in Schipluiden, The Netherlands in a glass-covered greenhouse in containers during the spring. During the production of the plants, day temperatures were about 26° C. and night temperatures were about 25° C. Plants used for the aforementioned photographs and following description were about one year old.

Botanical classification: *Bougainvillea spectabilis* cultivar Vera Pink.

Parentage: Naturally-occurring whole plant mutation of the *Bougainvillea spectabilis* cultivar Vera Deep Purple, disclosed in U.S. Plant Pat. No. 10,950.

Propagation:

*Type.*—By cuttings.

*Time to initiate roots.*—About 8 to 10 days at 25° C.

*Time to develop roots.*—About 10 to 14 days at 25° C.

*Root description.*—Fibrous and freely branching.

Plant description:

*Form.*—Upright, outwardly spreading and compact growth habit.

*Plant height, soil level to top of plant plane.*—About 24 cm.

*Plant width.*—About 21 cm.

*Lateral branch description.*—Quantity: About two or three per plant. Length: About 10.3 cm. Diameter: About 3 mm. Internode length: About 1.1 mm. Texture: Thornless; densely pubescent. Color: 144B.

*Foliage description.*—Arrangement: Alternate, simple. Length: About 7.4 cm. Width: About 3.6 mm. Shape: Elliptic to ovate. Apex: Acute to apiculate. Base: Attenuate. Margin: Entire; undulate. Texture, upper and lower surfaces: Smooth, glabrous. Luster, upper and lower surfaces: Moderately glossy. Venation pattern: Pinnate. Color: Developing foliage, upper surface: Between 137A and 143A. Developing foliage, lower surface: 137C. Fully expanded foliage, upper surface: Between 137A and 139A. Fully expanded foliage, lower surface: 137C. Venation, upper surface: 144A. Venation, lower surface: 144B. Petiole length: About 1.5 cm. Petiole diameter: About 1.5 mm. Petiole color: 143A to 143B.

Flower description:

*Flower type and habit.*—Single flowers arranged in axillary compound cymes with showy and colorful bracts; cymes roughly spherical. Flowers face outward and upright. Flowers not persistent.

*Fragrance.*—None.

*Natural flowering season.*—Continuously flowering from spring throughout the summer in Schipluiden, The Netherlands.

*Quantity.*—Freely flowering with about 21 flowers per cyme.

*Flower longevity on the plant.*—About one week.

*Inflorescence height.*—About 7.7 cm.

*Inflorescence diameter.*—About 8.5 cm.

*Flower diameter.*—About 7 mm.

*Flower depth* (*height*).—About 2 mm.

*Flower buds.*—Length: About 7 mm. Diameter: About 2 mm. Shape: Oblanceolate; apex, rounded. Color: 138B; towards the apex, 150D.

*Petals.*—Quantity per flower: About five; fused tubular corolla. Length: About 2 cm. Width: About 3.5 mm. Shape: Narrowly flabellate. Apex: Emarginate. Margin: Entire. Texture, upper and lower surfaces: Smooth; glabrous. Color: When opening and fully opened, upper surface: 150D; towards the center, 149A. When opening and fully opened, lower surface: 157D.

*Sepals.*—Quantity per flower: About five; fused tubular corona. Length: About 1.9 cm. Diameter: About 1.5 mm. Shape: Roughly lanceolate. Apex: Acute. Margin: Entire. Color: When opening, upper and lower surfaces: 138B. Fully opened, upper surface: 138B to 138C. Fully opened, lower surface: 138B.

*Pedicels.*—Length: About 1.4 cm. Diameter: About 1 mm. Angle: Erect to about 30° from vertical. Strength: Moderate. Color: 144A.

*Flower bracts.*—Quantity per flower. One; showy and colorful. Length: About 3.3 cm. Width: About 2.8 mm. Shape: Broadly ovate. Apex: Abruptly acute. Base: Cordate. Margin: Entire. Texture, upper and lower surfaces: Smooth; glabrous. Color: When opening, upper and lower surfaces: N66D. Fully opened, upper and lower surfaces: N66D to 70C; venation, 144A.

*Reproductive organs.*—Androecium: Stamens per flower: About eight. Stamen length: About 1.2 cm. Anther shape: Oval. Anther length: About 0.5 mm. Anther color: 13A. Pollen amount: Scarce. Pollen color: 13B to 13C. Gynoecium: Quantity of pistils per flower: One. Pistil length: About 4.5 mm. Stigma shape: Linear. Stigma color: N155A. Style length: About 1.5 mm. Style color: 144B. Ovary color: 144B.

*Seeds/fruits.*—Seed and fruit development has not been observed.

Disease/pest resistance: Under commercial production conditions, plants of the new *Bougainvillea* have not been noted to be resistant to pathogens or pests common to *Bougainvillea*.

Temperature tolerance: Plants of the new *Bougainvillea* have been observed to tolerate temperatures from 3 to 40° C. in Schipluiden, The Netherlands.

It is claimed:

1. A new and distinct cultivar of *Bougainvillea* plant named 'Vera Pink', as illustrated and described.

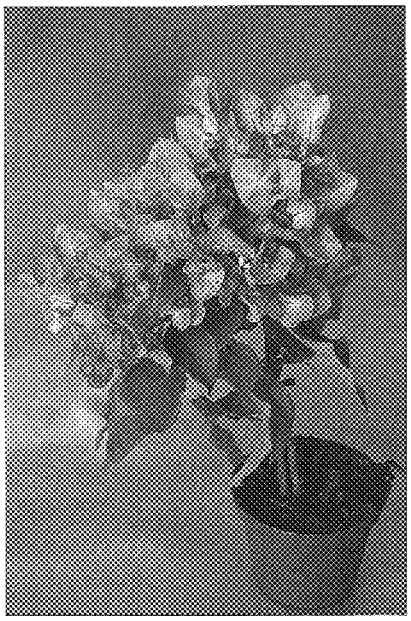
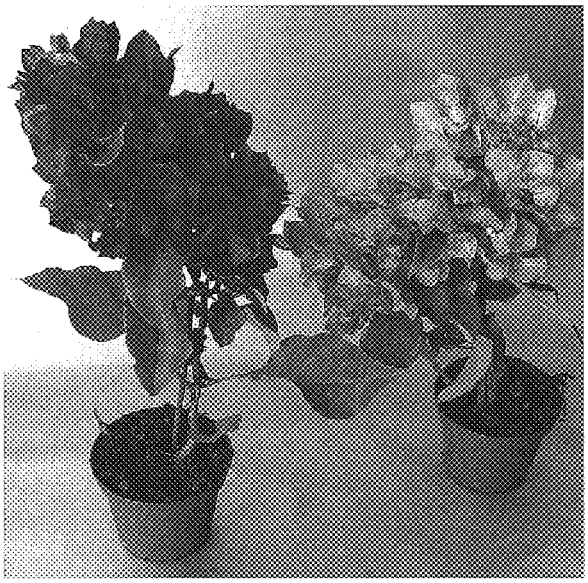

* * * * *